United States Patent
Akimoto et al.

(10) Patent No.: US 7,723,386 B2
(45) Date of Patent: May 25, 2010

(54) LIPID-IMPROVING AGENT AND COMPOSITION CONTAINING LIPID-IMPROVING AGENT

(75) Inventors: Kengo Akimoto, Kawasaki (JP); Harukazu Fukami, Kyoto (JP); Toshinao Goda, Shizuoka (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 735 days.

(21) Appl. No.: 10/550,711

(22) PCT Filed: Mar. 26, 2004

(86) PCT No.: PCT/JP2004/004282

§ 371 (c)(1), (2), (4) Date: Feb. 17, 2006

(87) PCT Pub. No.: WO2004/085582

PCT Pub. Date: Oct. 7, 2004

(65) Prior Publication Data

US 2006/0217441 A1  Sep. 28, 2006

(30) Foreign Application Priority Data

Mar. 27, 2003 (JP) ............................... 2003-088631

(51) Int. Cl.
*A01N 37/06* (2006.01)
(52) U.S. Cl. ...................................................... 514/547
(58) Field of Classification Search .................. 514/547
See application file for complete search history.

(56) References Cited

FOREIGN PATENT DOCUMENTS

| EP | 1 419 768 A1 | | 5/2004 |
| JP | 2002 180082 | * | 6/2002 |
| WO | WO 02/06505 | * | 1/2002 |
| WO | WO 03/004667 | * | 1/2003 |

OTHER PUBLICATIONS

Kawashima et al: "Enzymatic synthesis of high-purity structured lipids with caprylic acid at 1,3-positions and polyunsaturated fatty acid at 2- position" Journal of the American Oil Chemists' Society, American Oil Chemists' Society. Champaign, US, vol. 78, No. 6, 2001, pp. 611-616.*

(Continued)

*Primary Examiner*—Deborah D Carr
(74) *Attorney, Agent, or Firm*—Drinker Biddle & Reath LLP (57) ABSTRACT

A lipid-improving agent containing a triglyceride(s) where a poly-unsaturated fatty acid is bonded to 2-position of a triglyceride(s).

2 Claims, 5 Drawing Sheets

OTHER PUBLICATIONS

Namal et al., "Positional distribution of FA in TAG of enzymatically modified borage and evening primrose oils." Lipids, vol. 37, No. 8, 2002, pp. 803-810.*

Yoshida et al., Journal of Nutritional Science and Vitaminology., vol. 45, 1999, pp. 411-421.*

Database WPI, Section Ch, Week 200301, Derwent Publications Ltd., London, GB; AN 2003-003195 XP002293655 & JP 2002-180082 (Maruha Corp) Jun. 26, 2002 Abstract.

Akiko Kawashima et al., "Enzymatic Synthesis of High-Purity Structured Lipids with Caprylic Acid at 1,3-Positions and Polyunsaturated Fatty Acid at 2-Position", Journal of the American Oil Chemists' Society, vol. 78, No. 6, Jun. 2001, pp. 611-616.

Namal Senanayake, S.P.J., and Shahidi, "Positional Distribution of FA in TAG of Enzymatically Modified Borage and Evening Primrose Oils", Lipids, vol. 27, No. 8, 2002, pp. 803-810.

Hiroko Yoshida et al., "Effect of Dietary Seal and Fish Oils on Triacylglycerol Metabolism in Rats", Journal of Nutritional Science and Vitaminology, vol. 45, 1999, pp. 411-421.

International Search Report dated Aguust 24, 2004, issued in PCT/JP2004/004282 filed Mar. 26, 2004.

Office Action issued by the European Patent Office in EP Application No. 04 723 750.8-1221 dated Sep. 14, 2007.

* cited by examiner

Fig.1

Fig. 4

LIPID-IMPROVING AGENT AND COMPOSITION CONTAINING LIPID-IMPROVING AGENT

CROSS REFERENCE TO RELATED APPLICATIONS

This application is a national stage of PCT/JP2004/004282 filed Mar. 26, 2004, and claims benefit of Japanese Application No. 2003-088631 filed Mar. 27, 2003.

INDUSTRIAL FIELD

The present invention relates to a novel lipid-improving agent containing a poly-unsaturated fatty acid and having a structured lipid comprising a poly-unsaturated fatty acid.

BACKGROUND ART

Fat is an important nutrient the same as protein and saccharide and it is particularly useful as a high energy source. However, because fat is high in calories (9 kcal/g), it promotes obesity and is a cause for problems such as lifestyle-related illnesses. Actually, when hyperlipemia (hypercholesterolemia, hypertriglyceridemia) is found, a diet therapy is adopted as a first method of treatment and, when appropriate dietetic therapy and movement therapy are applied, the condition often improves and may become normalized. However, since fat enhances appetite, people today often eat foods containing large amounts of fat, and in advanced countries, where food is plentiful, excess fat intake is becoming a problem.

Most often, hypertriglyceridemia is a result of over eating, insufficient movement, obesity and excessive consumption of alcohol, and therefore, there are many cases where hypertension and diabetes mellitus occur as complications at the same time. Therefore, in many cases where there are multiple risk factors or where it is hard to improve daily lifestyle habits, in order to prevent the onset of ischemic heart diseases, a positive drug therapy is carried out.

With regard to drugs for hypertriglyceridemia, there are drugs of a fibrate type (in Japan, bezafibrate) (Bezatol SR® and Bezalip®) and fenofibrate (Lipantil®) are known as fibrate type drugs of the second generation. The main action of mechanism of the fibrate type drugs is mediated by activation of transcription factor α of an intranuclear receptor type (PPARα: peroxisome proliferator-activated receptor α).

Therefore, β-oxidation of fatty acid is promoted and production of hepatic triglyceride(s) lowers, and as a result, production of VLDL-TG is suppressed. In addition, activation of PPARα enhances an LPL activity and catabolism of triglyceride(s)-rich lipoprotein is accelerated. Further, an increase in the production of apo A I and A II and suppression of production of apo C III are induced. In addition, it has been noted that drugs of a fibrate type act to suppress cholesterol synthesis in the liver, promote sensitivity to insulin and promote discharge of cholesterol in bile. As a result, drugs of a fibrate type lower a triglyceride(s) concentration in serum by 20-50% and increase HDL-cholesterol by 10-15%.

As to other drugs, preparations of nicotinic acid (niceritrol (Perycit®) and nicomol (Cholexamin®)) have been found to be useful for hypertriglyceridemia and hyperglycemia of a mixed type (accompanied by hypertriglyceridemia, hypercholesterolemia and hypo-HDL-cholesterolemia). The main action mechanism of drugs of a nicotine type is that hepatic triglyceride(s) is lowered by inhibition of fatty acid synthesis, suppression of mobilization of fatty acid to the liver and suppression of esterification of hepatic fatty acid. At present, drugs of a fibrate type are used as the first choice, but in drug therapy, side effects such as hepatic function disorder, renal function disorder and myopathy must be noted. In addition, most side effects of drugs are expressed within six months after initiation of administration, and therefore, it is important to watch for the onset of side effects when the effectiveness of the drug is tested during the period of six months or, at least three to four months, after the administration is started or the dosage is increased. Accordingly, very careful attention is necessary during the administration of drugs, and it is not possible to administer such drugs for the purpose of prevention.

At present, as a preventive means, development of substitutes for fat/oil and non-absorbing fat/oil has been carried out, an example being sucrose fatty acid polyester (U.S. Pat. No. 3,600,186). Since it is discharged without being absorbed in vivo, the amount of calories derived from fat/oil is 0 kcal/g. However, absorption of fat-soluble vitamins is inhibited, and essential fatty acids are not supplied, and therefore, it is unable to be used as a commonly-used fat/oil. Under the circumstances, diacylglyceride has been developed in recent years as a source for supplying essential fatty acids.

In diacylglyceride, fatty acids are bonded mostly to 1,3-positions of a triglyceride(s), and upon being absorbed, fatty acids are cut out by a pancreatic lipase which is specific to 1,3-positions and the resulting glyceride and fatty acids are absorbed from the intestine. However, they are not reconstructed to a triglyceride(s) in epidermal cells of the small intestine but are absorbed with the portal vein and carried to the liver directly. Accordingly, accumulation of fat is suppressed. (In the case of a triglyceride(s), 2-acylmonoglyceride and fatty acid are absorbed in the intestine, reconstructed to a triglyceride(s) in epidermal cells of the small intestine, incorporated with chylomicron, secreted into lymph and circulate through the peripheral tissues.)

However, none of the developed fat/oil substitutes have the effect of drugs to burn fat in vivo (β-oxidation) and the effect is limited as well. Although inhibitors for pancreatic lipase to suppress absorption have been developed as well, their effect is also limited.

DISCLOSURE OF THE INVENTION

Therefore, there has been a strong demand for a compound which exhibits a lipid-improving action, is excellent for application to food and has little side effect.

Accordingly, the present invention is intended to provide a lipid-improving agent and beverage/food having a lipid-improving action containing, as an active ingredient, a triglyceride(s) where a poly-unsaturated fatty acid is bonded to 2-position of the triglyceride(s), or a triglyceride(s) where a poly-unsaturated fatty acid is bonded to 2-position and saturated fatty acid and/or mono-unsaturated fatty acid are/is bonded to 1,3-positions of the triglyceride(s), and to provide a method for producing the same.

More particularly, the object of the present invention is to provide a lipid-improving agent and beverage/food having a lipid-improving action or, to be more specific, which functions such that neutral fat (triglyceride(s)) and/or cholesterol in blood are/is lowered, DL-cholesterol in blood is increased, stored fat is burned (promotion of β-oxidation), edible fat is burned (promotion of β-oxidation), expression of hepatic PPARα which is a transcription factor of an intranuclear receptor type and/or related gene (such as hepatic β-oxidation enzyme gene) is enhanced and expression of PPARγ of fat tissues and/or related gene is suppressed, the lipid-improving agent containing an active ingradient, at least one member selected from a triglyceride(s) where poly-unsaturated fatty acid of omega-6 type, omega-3 type or omega-9 type is bonded to 2-position of the triglyceride(s) and a triglyceride(s) where poly-unsaturated fatty acid of omega-6 type, omega-3 type or omega-9 type is bonded to 2-position and saturated and/or mono-unsaturated fatty acid having not less than 8 carbons are/is bonded to 1,3-positions of the triglyceride(s), and to provide a method for producing the same.

The present inventors carried out a screening of components which activate a transcription factor of an intranuclear receptor type (PPAR) participating in lipid metabolism, a mechanism of drugs of a fibrate type which are the first choice for treatment of hypertriglyceridemia. It has been known that, when fat/oil is ingested, it enhances expression of PPARα mRNA and promotes absorption of fatty acid and vitamin A in epidermal cells of the small intestine, while in the liver, it enhances expression of PPARα mRNA and promotes β-oxidation of fatty acid. It has been also known that, as the PPAR ligand, poly-unsaturated fatty acid is more effective than saturated fatty and mono-unsaturated fatty acid. Therefore, the present inventors concentrated on poly-unsaturated fatty acid as a safe natural component which activates PPAR.

When fat/oil is absorbed, fatty acids bonded to 1,3-positions are cut out by a pancreatic lipase specific to 1,3-positions, and therefore, intensive studies were conducted based on the assumption that a triglyceride(s) where a poly-unsaturated fatty acid is bonded to 1,3-positions of the triglyceride(s) is an ideal triglyceride(s) structure. It was surprisingly found that a triglyceride(s) where poly-unsaturated fatty acid is bonded to 2-position of the triglyceride(s) and also a triglyceride(s) where poly-unsaturated fatty acid is bonded to 2-position and saturated fatty acid and/or mono-unsaturated fatty acid are/is bonded to 1,3-positions of the triglyceride(s), have greater activating action on PPAR. Since the poly-unsaturated fatty acid bonded to 2-position is not cut out by a 1,3-position-specific pancreatic lipase, it was assumed that PPAR is rarely activated, but the results of the inventors' studies were contrary to expectation, and found thus the present invention was arrived at.

Accordingly, the present invention is intended to provide a lipid-improving agent and beverage/food having a lipid-improving action which contains, as an active ingredient, a triglyceride(s) where a poly-unsaturated fatty acid is bonded to 2-position of the triglyceride(s), or a triglyceride(s) where a poly-unsaturated fatty acid is bonded to 2-position and saturated fatty acid and/or mono-unsaturated fatty acid are/is bonded to 1,3-positions of the triglyceride(s), and also to provide a method for producing the same.

More particularly, the present invention is intended to provide a lipid-improving agent and beverage/food having a lipid-improving action or, to be more specific, which functions such that neutral fat (triglyceride(s)) and/or cholesterol in blood are/is lowered, HDL-cholesterol in blood is increased, stored fat is burned (promotion of β-oxidation), edible fat is burned (promotion of β-oxidation), expression of hepatic PPARα which is a transcription factor of an intranuclear receptor type and/or related gene (such as hepatic β-oxidation enzyme gene) is enhanced and expression of PPARγ of fat tissues and/or related gene is suppressed, the lipid-improving agent containing, as an active ingredient, at least one member selected from a triglyceride(s) where poly-unsaturated fatty acid of omega-6 type, omega-3 type or omega-9 type is bonded to 2-position of the triglyceride(s) and a triglyceride(s) where poly-unsaturated fatty acid of omega-6 type, omega-3 type or omega-9 type is bonded to 2-position and saturated and/or mono-unsaturated fatty acid having not less than 8 carbons are/is bonded to 1,3-positions of the triglyceride(s), and also to provide a method for producing the same.

The present invention is able to provide a lipid-improving agent and beverage/food having a lipid-improving action containing, as an active ingredient, a triglyceride(s) where a poly-unsaturated fatty acid is bonded to 2-position of the triglyceride(s), or a triglyceride(s) where a poly-unsaturated fatty acid is bonded to 2-position and a saturated fatty acid and/or mono-unsaturated fatty acid are/is bonded to 1,3-positions of the triglyceride(s), and also to provide a method for producing the same. The present invention is particularly useful for humans in modern society.

EMBODIMENTS FOR CARRYING OUT THE INVENTION

The present invention relates to a lipid-improving agent and beverage/food having a lipid-improving action containing, as an active ingredient, a triglyceride(s) where a poly-unsaturated fatty acid is bonded to 2-position of the triglyceride(s), or a triglyceride(s) where a poly-unsaturated fatty acid is bonded to 2-position and a saturated fatty acid and/or mono-unsaturated fatty acid are/is bonded to 1,3-positions of the triglyceride(s), and also to providing a method for producing the same.

The compound of the present invention and a composition containing said compound are effective as beverage/food, health food, functional food, designated health food, food for babies, food for aged people, drugs, quasi-drug, etc. with a purpose of prevention and improvement, having a lipid-improving action, to be more specific, having such action that neutral fat (triglyceride(s)) and/or cholesterol are/is lowered, HDL-cholesterol in blood is increased, stored fat is burned (promotion of β-oxidation) and edible fat is burned (β-oxidation) and, in view of mechanisms, in lever, expression of PPARα which is a transcription factor of an intranuclear receptor type and/or related gene (such as acyl CoA oxidase and other enzymes in an β-oxidation system and an uncoupling protein (such as UCP-2)) is enhanced and expression of fatty acid synthetase (FAS) gene is suppressed, and, in fat cells, expression of PPARγ and/or related gene (such as fat cell-specific fat bonding protein (aP2) and an uncoupling protein (UCP-2)) is suppressed, expression of acyl CoA oxidase and other enzymes in a β-oxidation system and/or an uncoupling protein (UCP-2) gene is enhanced and expression of fatty acid synthetase (FAS) gene is suppressed.

The compound of the present invention is able to utilize a triglyceride(s) where a poly-unsaturated fatty acid is bonded to 2-position of the triglyceride(s) and also a triglyceride(s) where a poly-unsaturated fatty acid is bonded to 2-position and saturated fatty acid and/or mono-unsaturated fatty acid are/is bonded to 1,3-positions of the triglyceride(s).

Specific examples of the poly-unsaturated fatty acid bonding to 2-position are an unsaturated fatty acid of an omega-6 type (such as 9,12-octadecadienoic acid (linoleic acid) 18:2ω6, 6,9,12-octadecatrienoic acid (γ-linolenic acid), 18:3ω6, 8,11,14-eicosatrienoic acid (dihomo-γ-linolenic acid) 20:3ω6,5,8,11,14-eicosatrienoic acid (arachidonic acid), 20:4ω6, 7,10,13,16-docosatetraenoic acid 22:4ω6 or 4,7,10,13,16-docosapentaenoic acid 22:5ω6), an unsaturated fatty acid of an omega-3 type (such as 9,12,15-octadecatrienoic acid (α-linoleic acid) 18:3ω3, 6,9,12,15-octadecatetraenoic acid (stearidonic acid) 18:4ω3, 11,14,17-eicosatrienoic acid (dihomo-α-linolenic acid) 20:3ω3, 8,11,14,17-eicosatetraenoic acid 20:4ω3, 5,8,11,14,17-eicosapentaenoic acid 20:5ω3, 7,10,13,16,19-docosapentaenoic acid 22:5ω3 or 4,7,10,13,16,19-docosahexaenoic acid 22:6ω3) and an unsaturated fatty acid of an omega-9 type (such as 6,9-octadecadienoic acid 18:2ω9, 8,11-eicosadienoic acid 20:2ω9 or 5,8,11-eicosatrienoic acid (mead acid) 20:3ω9), but they are non-limitative and anything may be used so far as it is a poly-unsaturated fatty acid having not less than 18 carbons and not less than 2 double bonds. Examples of the saturated fatty acid and/or mono-unsaturated acid bonding to 1,3-positions are octanoic acid (caprylic acid) 8:0, decanoic acid (capric acid) 10:0, dodecanoic acid (lauric acid) 12:0, tetradecanoic acid (myristic acid) 14:0, hexadecanoic acid (palmitic acid) 16:0, octadecanoic acid (stearic acid) 18:0, 9-octadecanoic acid (oleic acid) 18:1ω9, arachidic acid 20:0 and behenic acid 22:0 although they are non-limitative and anything may be used so far as it is a saturated fatty acid or a mono-unsaturated fatty acid having not less than 8 carbons. It goes without saying that the fatty acids bonding to 1- and 3-positions are same or used in a combined manner.

Specific compounds are the following triglycerides such as 1,3-dipalmitoyl-2-arachidonoyl glyceride (16:0-20:4ω6-16:0), 1,3-dipalmitoyl-2-5,8,11,14,17-eicosapentanoyl glyceride (16:0-20:5ω3-16:0), 1,3-dipalmitoyl-2-4,7,10,13,16,19-docosahexanoyl glyceride (16:0-22:6ω3-16:0), 1,3-dipalmitoyl-2-dihomo-γ-linolenoyl glyceride (16:0-20:3ω6-16:0), 1,3-dipalmitoyl-2-meadnoyl glyceride (16:0-20:3ω9-16:0), 1,3-dicapryloyl-2-arachidonoyl glyceride (8:0-20:4ω6-8:0), 1,3-dicapryloyl-2-5,8,11,14,17-eicosapentanoyl glyceride (8:0-20:5ω3-8:0), 1,3-dicapryloyl-2-4,7,10,13,16,19-docosahexanoyl glyceride (8:0-22:6ω3-8:0), 1,3-dicapryloyl-2-dihomo-γ-linolenoyl glyceride (8:0-20:3ω6-8:0), 1,3-dicapryloyl-2-meadnoyl glyceride (8:0-20:3ω9-8:0), 1,3-dioleoyl-2-arachidonoyl glyceride (18:1ω9-20:4ω6-18:1ω9), 1,3-dioleoyl-2-5,8,11,14,17-eicosapentanoyl glyceride (18:1ω9-20:5ω3-18:1ω9), 1,3-oleoyl-2-4,7,10,13,16,19-docosahexanoyl glyceride (18:1ω9-22:6ω3-18:1ω9), 1,3-dioleoyl-2-dihomo-γ-linolenoyl glyceride (18:1ω9-20:3ω6-18:1ω9) and/or 1,3-dioleoyl-2-meadnoyl glyceride (18:1ω9-20:3ω9-18:1ω9) although they are non-limitative but anything may be utilized so far as it is a triglyceride(s) where poly-unsaturated fatty acid is bonded to 2-position of the triglyceride(s) or a triglyceride(s) where highly saturated fatty acid is bonded to 2-position and saturated fatty acid and/or mono-unsaturated fatty acid are/is bonded to 1,3-positions of the triglyceride(s).

One of the effective ingredient of the present invention is a triglyceride(s) where highly saturated fatty acid is bonded to 2-position and saturated fatty acid and/or mono-unsaturated fatty acid are/is bonded to 1,3-positions of the triglyceride(s) and may be prepared, for example, by the following means.

Thus, one of specific processes for the production of a triglyceride(s) where poly-unsaturated fatty acid is bonded to 2-position and saturated fatty acid and/or mono-unsaturated fatty acid are/is bonded to 1,3-positions of the triglyceride(s) is that lipase which acts only on ester bonds at 1,3-positions of a triglyceride(s) is made to act in the presence of fat/oil (triglyceride(s)) containing poly-unsaturated fatty acid as a constituting fatty acid and a saturated fatty acid and/or mono-unsaturated fatty acid.

The fat/oil (triglyceride(s)) used as a starting material is a triglyceride(s) containing poly-unsaturated fatty acid of an omega-6 type, a poly-unsaturated fatty acid of an omega-3 type and/or a poly-unsaturated fatty acid of an omega-3 type as a constituting fatty acid. When the rate of the poly-unsaturated fatty acid to the total fatty acid constituting the triglyceride(s) is high, the temperature for the enzymatic reaction is to be 30 to 50° C. or, preferably, 40 to 50° C. being higher than the usual enzymatic reaction temperature which is 20 to 30° C. in order to prevent a lowering of reaction yield as a result of an increase of the unreacted fat/oil (a starting triglyceride(s) and a triglyceride(s) where one of fatty acids at 1,3-positions becomes saturated fatty acid and/or mono-unsaturated fatty acid).

Examples of the lipase which specifically acts on the ester bond of 1,3-positions of the triglyceride(s) are those which are produced by microorganism such as genus *Rhizopus*, genus *Rhizomucor* and genus *Aspergillus* and pancreatic lipase of swine. With regard to the lipase as such, commercially available one may be used. Its examples are lipase of *Rhizopus delemar* (Talipase manufactured by Tanabe Seiyaku), lipase of *Rhizomucor miehei* (Ribozyme IM manufactured by Novo Nordisk) and lipase of *Aspergillus niger* (Lipase A manufactured by Amano Seiyaku) although they are non-limitative, and anything may be used so far as it is a lipase which is specific to 1,3-positions.

With regard to the form for use of the above lipase, it is desirable to use a lipase which is immobilized on an immobilizing carrier to impart a heat resistance to the enzyme because the reaction is carried out at a temperature of not lower than 30° C. or, preferably, not lower than 40° C. with a purpose of enhancing the reaction efficiency. With regard to the immobilizing carrier, an ion-exchange resin carrier which is a highly porous resin having a pore size of not smaller than about 100 Å such as Dowex Marathon WBA (a trade name; Dow Chemical) may be exemplified.

One part of the immobilizing carrier is suspended in 0.5 to 20 part(s) by weight of an aqueous solution of lipase specific to 1,3-positions and 2 to 5 parts of cold acetone (e.g., −80° C.) to the suspension are added thereto gradually with stirring whereupon a precipitate is formed. An immobilized enzyme can be prepared by drying the precipitate in vacuo.

In a simpler method, 0.05 to 0.4 part(s) of lipase specific to 1,3-positions to one part of an immobilizing carrier is/are dissolved in a minimum amount of water, the immobilizing carrier is mixed therewith with stirring and the mixture is dried in vacuo to prepare an immobilized enzyme. As a result of the operation as such, about 90% of lipase are carried on a carrier but the product as it is does not show transesterifying activity at all. Thus, when it is subjected to a pretreatment in a substrate (comprising starting fat/oil and medium-chain fatty acid) to which 1 to 10% (w/v) of water is/are added or, preferably, in a substrate to which 1 to 3% of water is/are added, the immobilized enzyme can be most efficiently activated and can be used for the manufacture.

In some types of enzymes, amount of water to be added to the present reaction system is very important. Thus, when no water is contained, the transesterifying reaction hardly proceeds while, when the amount of water is much, hydrolysis takes place and recovery rate of the glyceride lowers (when hydrolysis takes place, diglyceride and monoglyceride are produced). However, when an immobilized enzyme which is activated by means of a pretreatment is used in that case, the amount of water to be added to the present reaction system is no longer important and, even in a system containing no water at all, the transesterifying reaction is able to carried out efficiently. It is also possible to omit the pretreatment when the type of the enzyme preparation is duly selected.

When the heat-resistant immobilized enzyme as such is used and enzymatic reaction temperature is raised, it is now possible to efficiently manufacture a triglyceride(s) where saturated fatty acid and/or mono-unsaturated fatty acid is bonded to 1,3-positions and a highly saturated fatty acid is bonded to 2-position without lowering the reactivity even in the case of a fat/oil (triglyceride(s)) containing a poly-unsaturated fatty acid having low reactivity to lipase which is specific to 1,3-positions.

The fat/oil (triglyceride(s)) used as a starting material is a triglyceride(s) containing poly-unsaturated fatty acid of an omega-6 type, poly-unsaturated fatty acid of an omega-3 type and/or poly-unsaturated fatty acid of an omega-3 type, as a constituting fatty acid and examples of the triglyceride(s) where poly-unsaturated fatty acid of an omega 6 type is a constituting fatty acid are evening primrose oil (9,12-octadecadienoic acid (linoleic acid) and 6,9,12-octadecatrienoic acid (γ-linolenic acid)) and borage oil (9,12-octadecadienoic acid (linoleic acid) and 6,9,12-octadecatrienoic acid (γ-linolenic acid)). In addition, a process for an effective production of a triglyceride(s) where 5,8,11,14-eicosatetraenoic acid (arachidonic acid) and 8,11,14-eicosatrienoic acid (di-homo-γ-linoleic acid) are constituting fatty acids has been developed by the present inventors (P86-0087; JP-A-5-91887) and such a fat/oil may be also used as a starting fat/oil for an enzymatic reaction.

In the case of a triglyceride(s) where a poly-unsaturated fatty acid of an omega-9 type is a constituting fatty acid, a process for an effective production of a triglyceride(s) where 6,9-octadecadienoic acid 18:3ω9, 8,11-eicosadienoic acid 20:2ω9 or 5,8,11-eicosatrienoic acid (mead acid) 20:3ω9 is a constituting fatty acid has been developed by the present inventors (JP-A-5-91888, 10-57085 and 5-91886) and such a fat/oil may be also used as a starting fat/oil for an enzymatic reaction.

In the case of a triglyceride(s) where a poly-unsaturated fatty acid of an omega-3 type is a constituting fatty acid, fish oil such as tuna, bonito, sardine, mackerel, Pacific saury, cod, cuttlefish and horse mackerel may be used as a starting fat/oil for the enzymatic reaction. In fish oil, total fatty acid bonding to a triglyceride(s) is not always a poly-unsaturated fatty acid of an omega-3 type but, in some cases, a poly-unsaturated fatty acid of an omega-6 type is bonded as a constituting fatty acid. Fat/oil which is extracted from krill and algae such as *chlorella* and *spirulina* may also be used as a starting fat/oil for the enzymatic reaction.

It is also possible to use fat/oil prepared by incubation of a microorganism which has been known to produce a triglyceride(s) where 4,7,10,13,16,19-docosahexaenoic acid 22:6ω3 is a constituting fatty acid such as that belonging to genus *Crypthecodenium*, genus *Thraustochytrium*, genus *Schizochytrium*, genus *Ulkenia*, genus *Japonochytorium* or genus *Haliphthoros* as a starting fat/oil for the enzymatic reaction.

As a saturated fatty acid and/or a mono-unsubstituted fatty acid which are/is to be starting material(s), it is possible to use a saturated fatty acid and/or a mono-unsubstituted fatty acid extracted from vegetable fat/oil and a medium-chain fatty acid having 8 to 12 carbons as materials for the enzymatic reaction. In addition, the material may be subjected to the reaction as fatty acid, fatty acid salt, alcohol ester of fatty acid and/or triglyceride(s).

The active ingredient of the present invention is a triglyceride(s) where a poly-unsaturated fatty acid is bonded to 2-position and saturated fatty acid and/or mono-unsaturated fatty acid are/is bonded to 1,3-positions of the triglyceride(s) and it has been known that octanoic acid (caprylic acid) 8:0 and 9-octadecanoic acid (oleic acid) 18:1ω9 enhance the expression of PPAR gene and a triglyceride(s) whereby such fatty acids are bonded to 1,3-positions can be an effective lipid-improving agent.

A triglyceride(s) prepared by an enzymatic method is unable to give 100% triglyceride(s) having a lipid-improving action where a poly-unsaturated fatty acid is bonded to 2-position and saturated fatty acid and/or mono-unsaturated fatty acid are/is bonded to 1,3-positions of the triglyceride(s) but, from the gist of the invention, it is apparent that fat/oil (triglyceride(s)) containing not less than 5 mol %, preferably not less than 10 mol %, more preferably not less than 20 mol % and, most preferably, not less than 30 mol % of the said triglyceride(s) is also a triglyceride(s) having a lipid-improving action.

Incidentally, it is apparent that a process for the production of a triglyceride(s) where a poly-unsaturated fatty acid is bonded to 2-position and saturated fatty acid and/or mono-unsaturated fatty acid are/is bonded to 1,3-positions is not limited to an enzymatic synthesis but any process including chemical synthesis is able to be used.

In a process for the production of a composition having a lipid-improving action, a triglyceride(s) where a poly-unsaturated fatty acid is bonded to 2-position and saturated fatty acid and/or mono-unsaturated fatty acid are/is bonded to 1,3-positions may be compounded, either solely or jointly, with a food material which does not substantially contains a triglyceride(s) where a poly-unsaturated fatty acid is bonded to 2-position and saturated fatty acid and/or mono-unsaturated fatty acid are/is bonded to 1,3-positions or, if contained, the amount is little. Here, the expression that the amount is little means that, even when a triglyceride(s) where a poly-unsaturated fatty acid is bonded to 2-position and saturated fatty acid and/or mono-unsaturated fatty acid are/is bonded to 1,3-positions is contained in a material for beverage/food, when the food composition compounded therewith is ingested by human being, the amount is still below the ingesting amount of the poly-unsaturated fatty acid per day of the present invention which will be mentioned later.

The compound of the present invention is a triglyceride(s) and there is an unlimited possibility concerning its use. The compound may be used as a material for food, beverage, drug and quasi-drug and an additive thereto. There is no limitation at all for its purpose of use and amount of use.

Besides the general food, examples of the food composition are functional food, nutritional supplement, prepared milk for premature babies, prepared milk for babies, food for babies, food for expectant and nursing mothers and food for aged people. Examples of the food containing fat/oil are natural food which inherently contains fat/oil such as meat, fish and nut; food to which fat/oil is added upon cooking such as soup; food for which fat/oil is used as a heating medium such as doughnut; fat/oil food such as butter; processed food to which fat/oil is added upon processing such as cookie; and food to which fat/oil is sprayed or applied upon finishing the process such as hard biscuit. It is also possible to add to agricultural food, fermented food, livestock food, sea food or beverage which does not contain fat/oil. In addition, the form of functional food, drug and quasi-drug may be acceptable and it may be in a processed form such as enteral nutrient, powder, granule, troche, oral liquid, suspension, emulsion and syrup.

In addition to the effective ingredient of the present invention, the composition of the present invention may contain various carriers and additives which are commonly used for beverage/food, drug or quasi-drug. It is particularly preferred to contain an antioxidant to prevent the oxidation of the effective ingredient of the present invention. Examples of the antioxidant are natural ones such as tocopherols, flavone derivatives, phyllodulcins, kojic acid, gallic acid derivatives, catechins, fukiic acid, gossypol, pyrazine derivatives, sesamol, guaiaol, guaiacic acid, p-coumalic acid, nor-dihydroguaiaretic acid, sterols, terpenes, nucleic acid bases, carotenoids and lignans and synthetic ones represented by ascorbic palmitate, ascorbic stearate, butylhydroxyanisole (BHA), butylhydroxytoluene (BHT), mono-tert-butylhydroquinone (TBHQ) and 4-hydroxymethyl-2,6-di-tert-butylphenol (HMBP). Examples of the tocopherols are α-tocopherol, β-tocopherol, γ-tocopherol, δ-tocopherol, ε-tocopherol, ξ-tocopherol, η-tocopherol and tocopherol ester (such as tocopherol acetate). Examples of the carotenoids are β-carotene, canthaxanthin and astaxanthin.

Besides the effective ingredient of the present invention, the composition of the present invention may contain a carrier such as various carriers, extender, diluent, filler, dispersing agent, excipient, binder solvent (such as water, ethanol and vegetable oil), dissolving aid, buffer, dissolving promoter, gelling agent, suspending agent, wheat flour, rice powder, starch, corn starch, polysaccharide, milk protein, collagen, rice oil and lecithin, and additive such as vitamin compound, sweetener, organic acid, coloring agent, perfume, moisture preventer, fiber, electrolyte, mineral, nutrient, antioxidant, preservative, aromatic agent, moisturizer and natural food extract and vegetable extract although they are non-limitative.

Although the compound of the present invention is in a form of a triglyceride(s), active substance is a poly-unsaturated fatty acid bonded to 2-position of a triglyceride(s) which is a ligand for the transcription factor of an intranuclear receptor type (PPAR). It has been reported that ingesting amount of arachidonic acid from food per day is 0.14 g in Kanto District and 0.19 to 0.20 g in Kansai District (*Shishitsu Eiyogaku*, 4, 73-82, 1995) and the corresponding amount or more may be a yardstick for the ingestion of arachidonic acid.

Therefore, the daily ingesting amount of a triglyceride(s) where arachidonic acid is bonded to 2-position of triglyceride(s) or a triglyceride(s) where arachidonic acid is bonded to 2-position and saturated fatty acid and/or mono-unsaturated fatty acid are/is bonded to 1,3-positions of the triglyceride(s) for an adult (such as that having a body weight of 60 kg) in terms of the amount of arachidonic acid is 0.001 to 20 g, preferably 0.01 to 10 g, more preferably 0.05 to 5 g or, most preferably, 0.1 to 2 g. It has been reported that the daily ingesting amounts of 5,8,11,14,17-eicosapentaenoic acid 20:5ω3, 7,10,13,16,19-docosapentaenoic acid 22:5ω3 and 4,7,10,13,16,19-docosahexaenoic acid 22:6ω3 docosahexaenoic acid are 0.15, 0.05 and 0.27-0.37, respectively in Kanto District and are 0.35, 0.12-0.14 and 0.69-0.82, respectively in Kansai District and the corresponding amount or more may be a yardstick for the ingestion of arachidonic acid.

When a triglyceride(s) where a poly-unsaturated fatty acid is bonded to 2-position of the triglyceride(s), a triglyceride(s) where a poly-unsaturated fatty acid is bonded to 2-position and saturated fatty acid and/or mono-unsaturated fatty acid are/is bonded to 1,3-positions of the triglyceride(s) and fat/oil (triglyceride(s)) containing said triglyceride(s) are actually applied to beverage/food, an absolute amount of the poly-unsaturated fatty acid which is to be compounded with the food is also important.

However, the absolute amount to be compounded with beverage/food also varies depending upon the ingesting amount of the beverage/food to be compounded and, therefore, it is compounded in an amount of not less than 0.003% by weight, preferably not less than 0.03% by weight or, more preferably, not less than 0.3% by weight in terms of the amount of poly-unsaturated fatty acid. In addition, when a triglyceride(s) where a arachidonic acid is bonded to 2-position of the triglyceride(s) or a triglyceride(s) where arachidonic acid is bonded to 2-position and saturated fatty acid and/or mono-unsaturated fatty acid are/is bonded to 1,3-positions of the triglyceride(s) is compounded, it is used at an amount not less than 0.001% by weight, preferably not less than 0.01% by weight or, more preferably, not less than 0.1% by weight.

When the composition of the present invention is used as a drug, it is manufactured by a method which is common in the field of pharmaceutical preparations such as a method mentioned in the Japanese Pharmacopoeia or a method similar thereto.

When the composition of the present invention is used as a drug, the compounding amount of the effective ingredient in the composition is not particularly limited so far as the object of the present invention is achieved but an appropriate compounding rate may be used.

When the composition of the present invention is used as a drug, it is preferred to administer in a form of unit dosage form and an oral administration is particularly preferred. Dose of the composition of the present invention may vary depending upon age, body weight, symptom, frequency of administration, etc. and it is recommended that, for example, a triglyceride(s) where a poly-unsaturated fatty acid is bonded to 2-position of the triglyceride(s) or a triglyceride(s) where a poly-unsaturated fatty acid is bonded to 2-position and saturated fatty acid and/or mono-unsaturated fatty acid are/is bonded to 1,3-positions of the triglyceride(s) is administered per day to an adult (about 60 kg) in an amount of usually about 0.001 to 20 g, preferably about 0.01 to 10 g, more preferably about 0.05 to 5 g or, most preferably, about 0.1 to 2 g in terms of amount of the poly-unsaturated fatty acid by dividing into one to three times a day.

EXAMPLES

The present invention will now be more specifically illustrated by way of the following Examples although the present invention is not limited to the following Examples.

Example 1

Process for the Production of a Triglyceride(s) where Arachidonic Acid is Bonded to 2-position of the Triglyceride(s)

*Nortierella alpine* was used as an arachidonic acid-producing microorganism. A medium (6 kL) containing 1.8% of glucose, 3.1% of defatted soybean powder, 0.1% of soybean oil, 0.3% of $KH_2PO_4$, 0.1% of $Na_2SO_4$ 0.05% of $CaCl_2.2H_2O$ and 0.05% of $MgCl_2.6H_2O$ was prepared in a 10-kL culture vessel and the initial pH was adjusted to 6.0. The pre-cultured solution (30 L) was inoculated and subjected to an aeration culture with stirring for 8 days under the condition where temperature was 26° C., aeration was 360 $m^3$/hour and inner pressure of vessel was 200 kPa. The stirring was adjusted so as to keep the dissolved oxygen concentration 10 to 15 ppm.

With regard to a glucose concentration, the concentration within a medium was made within a range of 1 to 2.5% until the fourth day by means of a flowing-down method and, after that, it was kept at 0.5 to 1% (% hereinabove means weight (w/v) %). After completion of the culture, cells containing a triglyceride(s) where arachidonic acid is a constituting fatty acid is recovered by filtration and drying and fat/oil was extracted from the resulting cells with hexane and subjected to purifying steps for edible fat/oil (degumming, deacidifying, deodoring and decoloring) to give 150 kg of arachidonic acid-containing triglyceride(s) (where arachidonic acid was bonded to any position of the triglyceride(s)). The resulting fat/oil (triglyceride(s)) was made into a methyl ester and the resulting fatty acid methyl ester was analyzed by a gas chromatography whereupon the rate of arachidonic acid in the total fatty acid was 40.84%.

Incidentally, palmitic acid, stearic acid, oleic acid, linoleic acid, γ-linolenic acid and di-homo-γ-linolenic acid were 11.63%, 7.45%, 7.73%, 9.14%, 2.23% and 3.27%, respectively. Incidentally, the rate of a poly-unsaturated fatty acid at 2-position of a triglyceride(s) by a conventional analysis was 91.5% while that of arachidonic acid was 64.7%. Further, the above arachidonic acid-containing fat/oil (triglyceride(s)) was made into an ethyl ester and a fatty acid ethyl ester mixture containing 40% of ethyl arachidonate was subjected to a conventional high-performance liquid chromatography to separate and purity 99% ethyl arachidonate. The resulting ethyl arachidonate was subjected to a conventional saponification reaction to prepare free arachidonic acid.

Example 2

Chemical Synthesis of a Triglyceride(s) (XPX) where Saturated Fatty Acid and/or Mono-unsaturated Fatty Acid (X) are/is Bonded to 1,3-positions and a Poly-unsaturated Fatty Acid (P) is Bonded to 2-position and a Triglyceride(s) (PXX) where a Poly-unsaturated Fatty Acid (P) is Bonded to 1-position and Saturated Fatty Acid and/or Mono-unsaturated Fatty Acid (X) are/is Bonded to 2,3-positions or a Triglyceride(s) (XXP) where a Poly-unsaturated Fatty Acid (P) is Bonded to 3-position and Saturated Fatty Acid and/or Mono-unsaturated Fatty Acid (X) are/is Bonded to 1,2-positions Synthesis of 8A8 (1,3-dioctanoyl-2-arachidonoyl glyceride)

A dihydroxyacetone dimer (1 g, 0.55 mmol) was dissolved in 20 ml of methylene chloride, then 3.5 ml (2.2 mmol) of n-octanoic acid and 70 mg of dimethylaminobenzene were added thereto and, under cooling with ice, 4.6 g (1.2 mmol) of WS-DCC were added. After 2 hours, the mixture was concentrated and extracted with ethyl acetate and the extract was washed with water, 1N HCl and a saturated saline solution successively. After it was dried over anhydrous magnesium sulfate, it was concentrated in vacuo and the resulting residue was crystallized from cold hexane to give 3 g (8.7 mmol) of 1,3-dioctanoyloxyacetone (yield: 79%).

The ocatanoate (10.8 g, 31.5 mmol) was dissolved in 120 ml of THF, 8 ml of water were added, the mixture was strongly stirred with ice-cooling and 1.2 g (31.7 mmol) of sodium borohydride were added thereto little by little together with making the pH neutral with acetic acid. After completion of the addition, water which was made slightly acidic with 1N HCl was added, the mixture was extracted with ethyl acetate and the extract was washed with water and a saturated saline solution, dried over anhydrous magnesium sulfate and concentrated in vacuo. The resulting oily substance was dissolved in 100 ml of methylene chloride, then 300 mg of dimethylaminobenzene and 8 g (26.4 mmol) of arachidonic acid were added thereto and the mixture was cooled with ice. WS-DCC (6.5 g, 34.4 mol) was further added thereto followed by stirring for 1 hour.

The reaction solution was concentrated and extracted with ethyl acetate and the extract was successively washed with water, 1N HCl and a saturated saline solution. It was then dried over anhydrous magnesium sulfate and concentrated in vacuo and the resulting residue was subjected to a silica gel chromatography using hexane-ethyl acetate (9:1) to give 13.5 g (yield: 68%) of 8A8 which was an oily substance. PMR ($CDCl_3$) δ: 0.8-1.0 (9H, m), 1.2-1.4 (22H, m), 1.6-1.8 (6H, m), 2.0-2.2 (4H, m), 2.3-2.4 (6H, m), 2.7-2.9 (6H, m), 4.14 (2H, q), 4.29 (2H, q), 5.2-5.5 (9H, m).

Synthesis of 88A (1(3),2-dioctanoyl-3(1)-arachidonoyl glyceride (RS)-2,2-Dimethyl-1,3-dioxolane-4-methanol (5 g, 37.8 mmol) was dissolved in 50 ml of DMF and, under cooling with ice, 1.6 g (39.7 mmol) of a 60% dispersion of sodium hydride in oil were added little by little. After completion, the mixture was stirred for 10 minutes and 4.5 ml (37.8 mmol) of benzyl bromide were dropped thereinto. After that, the mixture was stirred for 5 hours. After completion of the reaction, water was added, the mixture was extracted with ethyl acetate and the extract was washed with water and a saturated saline solution. This was dried over anhydrous magnesium sulfate and concentrated in vacuo and the resulting oily substance was subjected to a silica gel chromatography with hexane-ethyl acetate (9:1) to give 6.5 g (yield: 77%) of 1(3),2-isopropylidene-3(1)-henzyloxyglyceride which was an oily substance. This substance (5.6 g, 25.2 mmol) was dissolved in 30 ml of acetic acid, 30 ml of water were added and the mixture was made to react at 60° C. for 1 hour.

After the reaction solution was concentrated in vacuo, the residue was extracted with ethyl acetate and the extract was washed with a saturated aqueous solution of sodium bicarbonate and a saturated saline solution. This was dried over anhydrous magnesium sulfate and concentrated in vacuo to give 3.9 g of an oily product (yield: 85%). This product (3.8 g, 20.9 mmol) was dissolved in 40 ml of methylene chloride, 6.9 ml (43.9 mmol) of n-octanoic acid and 150 mg of dimethylaminobenzene were added and, under cooling with ice, 8.7 g (46 mmol) of WS-DCC were added. After 2 hours, the mixture was concentrated and extracted with ethyl acetate and the extract was washed with water, 0.5N NaOH and a saline solution successively. This was dried over anhydrous magnesium sulfate and concentrated in vacuo to give 9.9 g of an oily product. This was dissolved in 100 ml THF-25 ml acetic acid, then 1.3 g of 10% palladium-carbon were added and a reaction was carried out through one night in the presence of hydrogen. After the catalyst was filtered off, the filtrate was concentrated in vacuo and extracted with ethyl acetate and the extract was washed with a saturated aqueous solution of sodium bicarbonate and a saturated saline solution.

After drying over anhydrous magnesium sulfate, it was concentrated in vacuo and the resulting residue was subjected to a silica gel chromatography with hexane-ethyl acetate (9:1) to give 6 g of a debenzylated product (yield: 83%). The debenzylated product (136 mg, 0.39 mmol) was dissolved in 3 ml of methylene chloride, 100 mg (0.33 mmol) of arachidonic acid and 3 mg of dimethylaminobenzene were added and, under cooling with ice, 90 mg (0.48 mmol) of WS-DCC were added. After 2 hours, the mixture was concentrated, extracted with ethyl acetate and the extract was washed with water, 1N HCl and a saturated saline solution successively. After drying over anhydrous magnesium sulfate, it was concentrated in vacuo and the resulting residue was subjected to a silica gel chromatography with hexane-ethyl acetate (9:1) to give 180 mg of an oily product (yield: 74%).

PMR (CDCl$_3$) δ: 0.8-1.0 (9H, m), 1.2-1.4 (22H, m), 1.5-1.8 (6H, m), 2.0-2.2 (4H, m), 2.3-2.4 (6H, m), 2.7-2.9 (6H, m), 4.1-4.2 (2H, m), 4.28 (2H, q), 5.3-5.5 (9H, m).

PAP (1,3-dipalmitoyl-2-arachidonoyl glyceride), PPA (1(3),2-dipalmitoyl-3(1)-arachidonoyl glyceride) and 8P8 (1,3-dioctaoyl-2-arachidonoyl glyceride) were also able to be prepared by the same method as in the case of 8A8 and 88A.

Example 3

Production of Triglyceride(s) Containing Not Less than 5% of Triglyceride(s) (8A8) where Medium-chain Fatty Acid is Bonded to 1,3-positions and Arachidonic Acid is Bonded to 2-position An ion-exchange resin carrier (Dowex Marathon WBA; Dow Chemical; Trade Mark) (100 g) was suspended in 80 ml of a 12.5% aqueous solution of *Rhizopus delemar* lipase (Talipase Powder; Tanabe Seiyaku) and dried in vacuo to give an immobilized lipase.

After that, a reaction was carried out using 80 g of the triglyceride(s) (TGA 40S) containing 40% by weight of arachidonic acid prepared in Example 1, 160 g of caprylic acid, 12 g of the above immobilized lipase and 4.8 ml water at 30° C. for 48 hours with stirring (130 rpm).

After completion of the reaction, the reaction solution was removed to give an activated immobilized lipase.

Then the immobilized lipase (*Rhizopus delemar* lipase; carrier: Dowex Marathon WBA, trade mark) (10 g) was filled in a glass column (1.8×12.5 cm; volume: 31.8 ml) equipped with a jacket, a mixed fat/oil where TGA 40S prepared in Example 1 and caprylic acid were mixed in 1:2 was flown into the column at a predetermined flow rate (4 ml/hour) and a continuous reaction was carried out to give 400 g of a reacted fat/oil. In the meanwhile, temperature of the column was kept at 40 to 41° C. From the resulting reacted fat/oil, unreacted caprylic acid and free fatty acids were removed by means of a molecular distillation followed by subjecting to purifying steps for edible fat/oil (degumming, deacidifying, deodoring and decoloring) to give a fat/oil (triglyceride(s)) containing 8A8.

When the rate of 8A8 in the 8A8-containing fat/oil (triglyceride(s)) prepared by gas chromatography and high-performance liquid chromatography was checked, it was 31.6% (Incidentally, the rates of 8P8, 8O8, 8L8, 8G8 and 8D8 were 0.6, 7.9, 15.1, 5.2 and 4.8%, respectively).

Fatty acids P, O, L, G and D bonding to 2-position of the triglyceride(s) were palmitic acid, oleic acid, linoleic acid, γ-linolenic acid and dihomo-γ-linolenic acid, respectively while 8P8 was 1,3-capryloyl-2-palmitoyl-glyceride, 8O8 was 1,3-capryloyl-2-oleoyl-glyceride, 8L8 was 1,3-caproloyl-2-linolenoyl-glyceride, 8G8 was 1,3-capryloyl-2-γ-linolenoyl-glyceride and 8D8 was 1,3-capryloyl-2-dihomo-γ-linolenonyl-glyceride). Incidentally, the resulting 8A8-containing fat/oil (triglyceride(s)) was subjected to a conventional high-performance liquid chromatography to separate and purify 96 mol % of 8A8.

Example 4

Adjustment of Expression of Lipid Metabolism Gene by Fat/Oil where Arachidonic Acid is Bonded to 2-position of Triglyceride(s)

Influence of fat/oil (arachidonic acid-containing fat/oil) where arachidonic acid is bonded to 2-position of a triglyceride(s) prepared in Example 1 on expression of gene related to lipid metabolism was tested using rats. Male rats of SD strain of 6 weeks age were divided into four groups. The arachidonic acid-containing fat/oil prepared in Example 1 was appropriately compounded with beef tallow, olive oil and corn oil to prepare four kinds of fat/oil as shown in Table 1 (0% AA, 14.6% AA, 26.8% AA and 37.7% AA) where arachidonic acid content was different and the experimental food shown in Table 2 (0% AA, 1% AA, 2.5% AA and 5% AA) was given for two weeks. The present experimental food was prepared in such a manner that the rate of arachidonic acid in the experimental food was made 0, 1, 2.5 and 5% while the rate of main fatty acids other than arachidonic acid in the experimental food was nearly the same (Table 3).

Ingestion of the food was conducted by a pair-feeding and body weight was measured every day. The experimental food was prepared using agar so that the daily ingested energy became same among each of the experimental food groups. After two weeks from ingestion of the experimental food, rats were killed by decapitation, the collected jejunum was perfused with a physiological saline solution which was treated with ice-cooled diethyl pyrocarbonate to remove the content therein, water was removed therefrom and then its weight was measured. With regard to liver and epididymis white fat tissues, weight of the whole tissues was measured. Further, according to a method of Chomezynski, et al., total RNA was extracted and prepared from each 100 mg of central jejunum, liver and epididymis white fat tissue and used for the measurement of expression of gene. In addition, blood upon killing by decapitation was collected and triglyceride(s) concentration and total cholesterol concentration in a serum fraction were quantified using a measuring kit (Triglyceride(s) E-Test Wako and Total Cholesterol E-Test Wako being used, respectively).

Total RNA (10 μg or 30 μg) extracted from each tissue was subjected to an electrophoresis using 1% agarose gel containing 2.2M of formaldehyde gel and transferred to a nylon membrane (Hybond N+; Amersham) by 20×SSC buffer for one night. The membrane to which the total RNA was transferred was pre-hybridized at 42° C. for 2 hours using an Ultrahyb hybridization solution (Ambion) and then subjected to hybridization at 42° C. for not shorter than 16 hours using each cDNA probe labeled with $^{32}P$ by a random primer method.

After completion of the hybridization, the membrane was incubated using a washing solution I (2×SSPE, 0.5% SDS) at 42° C. for 10 minutes (twice), then incubated using a washing solution III (0.1×SSPE, 0.5% SDS) at 42° C. for 15 minutes (once) and the membrane was washed. The surface of the washed membrane was exposed to light to an imaging plate (Fuji Photo Film) for 1 to 2 days and intensity of signal of mRNA on the membrane was analyzed by a bioimage analyzer BAS 200 (Fuji Photo Film).

Each of the measured results was expressed in terms of mean value±standard error, the resulting data were tested by a dispersion analysis and the result where significance difference was noted thereby was subjected to a multigroup test according to Tukey. That where the ratio of risk was not more than 5% was considered to be significant.

TABLE 1

Fatty Acid Compositions of Four Kinds of Fat/Oil Having Different Arachidonic Acid Contents

| Fat/Oil | 0% AA | 14.6% AA | 26.8% AA | 37.7% AA |
|---|---|---|---|---|
| Beef tallow | 52.0 | 34.7 | 19.4 | 0 |
| Olive oil | 0 | 2.9 | 4.3 | 10.6 |
| Arachidonic acid-containing fa/oil | 0 | 32.9 | 60.2 | 84.8 |
| Corn oil | 48.0 | 29.4 | 16.1 | 4.5 |
| Total (g) | 100.0 | 100.0 | 100.0 | 100.0 |
| Myristic acid (14:0) | 1.0 | 0.8 | 0.6 | 0.4 |
| Palmitic acid (16:0) | 15.4 | 13.9 | 12.6 | 10.7 |
| Palmitoleic acid (16:1) | 1.6 | 1.1 | 0.7 | 0.1 |
| Stearic acid (18:0) | 11.8 | 10.2 | 8.7 | 6.4 |
| Oleic acid (18:1ω9) | 37.0 | 28.1 | 20.1 | 14.7 |
| Linoleic acid (18:2ω2) | 26.0 | 18.8 | 13.9 | 9.8 |
| α-Linolenic acid (18:3ω3) | 1.1 | 0.7 | 0.4 | 0.2 |
| γ-Linolenic acid (18:3ω6) | 0 | 0.1 | 0.2 | 0.3 |
| DGLA (20:3ω6) | 0 | 1.1 | 2.0 | 2.8 |
| Arachidic acid (20:0) | 0.2 | 1.1 | 1.9 | 2.6 |
| Arachidonic acid (10:4ω6) | 0 | 14.6 | 26.8 | 37.7 |
| Others | 5.8 | 9.2 | 12.1 | 14.3 |

DGLA: Di-homo-γ-linolenic acid
DGLA: Di-homo-γ-linolenic acid

TABLE 2

Component Compositions of Experimental Food

| g/kg | 0% AA | 1% AA | 2.5% AA | 5% AA |
|---|---|---|---|---|
| Casein (Vitamin-free) | 159 | 159 | 159 | 159 |
| β-Corn starch | 479 | 439 | 383 | 295 |
| 0% AA Mixed fat/oil | 50 | | | |
| 14.6% AA Mixed fat/oil | | 68 | | |
| 26.8% AA Mixed fat/oil | | | 93 | |
| 37.7% AA Mixed fat/oil | | | | 132 |
| Minerals AIN-76 | 28 | 28 | 28 | 28 |
| Vitamins AIN-76 | 8 | 8 | 8 | 8 |
| DL-Methionine | 2 | 2 | 2 | 2 |
| Choline bitartrate | 2 | 2 | 2 | 2 |
| 2% Agar | 272 | 294 | 325 | 374 |

TABLE 3

Rate of Each Fatty Acid in Experimental Food (%)

| | 0% AA | 1% AA | 2.5% AA | 5% AA |
|---|---|---|---|---|
| Myristic acid (14:0) | 0 | 0.1 | 0.1 | 0 |
| Palmitic acid (16:0) | 0.8 | 0.9 | 1.2 | 1.4 |
| Palmitoleic acid (16:1) | 0.1 | 0.1 | 0.1 | 0 |
| Stearic acid (18:0) | 0.6 | 0.7 | 0.8 | 0.8 |
| Oleic acid (18:1ω9) | 1.9 | 1.9 | 1.9 | 1.9 |
| Linoleic acid (18:2ω2) | 1.3 | 1.3 | 1.3 | 1.3 |
| α-Linolenic acid (18:3ω3) | 0.1 | 0 | 0 | 0 |
| γ-Linolenic acid (18:3ω6) | 0 | 0 | 0 | 0 |
| DGLA (20:3ω6) | 0 | 0.1 | 0.2 | 0.4 |
| Arachidic acid (20:0) | 0 | 0.1 | 0.2 | 0.3 |
| Arachidonic acid (20:4ω6) | 0 | 1.0 | 2.5 | 5.0 |
| Others | 0.3 | 0.6 | 1.1 | 1.9 |

DGLA: Di-homo-γ-linolenic acid
DGLA: Di-homo-γ-linolenic acid

Influence on tissue weight and serum lipid concentration after 2 weeks of ingestion of the experimental food is shown in Table 4. Weight of epididymis white fat tissues corresponding to inner visceral fat lowered corresponding to the arachidonic acid amount in the experimental food and, in a 5% AA experimental food, the decrease was significant. In addition, serum total cholesterol and triglyceride(s) concentrations significantly lowered corresponding to the arachidonic acid amount in the experimental food. Lowering of the serum triglyceride(s) concentration was particularly significant and, in a group of 1% AA food, the lowering was 53% of a group of 0% AA food. Incidentally, under the condition of the present experimental raising loaded with arachidonic acid, no abnormal symptom such as inflammation caused by production of excessive eiconoside was observed and it was confirmed that there was no problem at all so far as arachidonic acid is ingested as a constituting fatty acid for a triglyceride(s).

TABLE 4

Influence of Ingestion of Experimental Food on Body Weight Increase, Relative Tissue Weight and Serum Lipid Concentration in Rats

|  | 0% AA | 1% AA | 2.5% AA | 5% AA |
|---|---|---|---|---|
| Body weight increase (g/14 days) | 91 ± 3 | 90 ± 7 | 89 ± 10 | 80 ± 5 |
| Ingested amount (g/day) | 27.5 ± 0.3 | 26.2 ± 0.7 | 27.4 ± 0.6 | 26.2 ± 0.6 |
| Liver weight (g/100 g body weight) | 4.0 ± 0.1 | 3.7 ± 0.3 | 4.0 ± 0.4 | 4.2 ± 0.1 |
| Epididymis fat tissue weight (g/100 g body weight) | 1.7 ± 0.1$^a$ | 1.4 ± 0.1$^{ab}$ | 1.4 ± 0.1$^{ab}$ | 1.2 ± 0.1$^b$ |
| Serum triglyceride(s) concn (μmol/dl) | 242 ± 19.7$^a$ | 128 ± 20.3$^b$ | 112 ± 12.8$^b$ | 87.0 ± 12.3$^b$ |
| Serum total cholesterol concn (μmol/dl) | 257 ± 6.25$^a$ | 239 ± 19.2$^a$ | 209 ± 16.5$^b$ | 144 ± 14.2$^b$ |

$^{a,b}$significant difference noted between different alphabets ($p < 0.05$)

Figure 1:
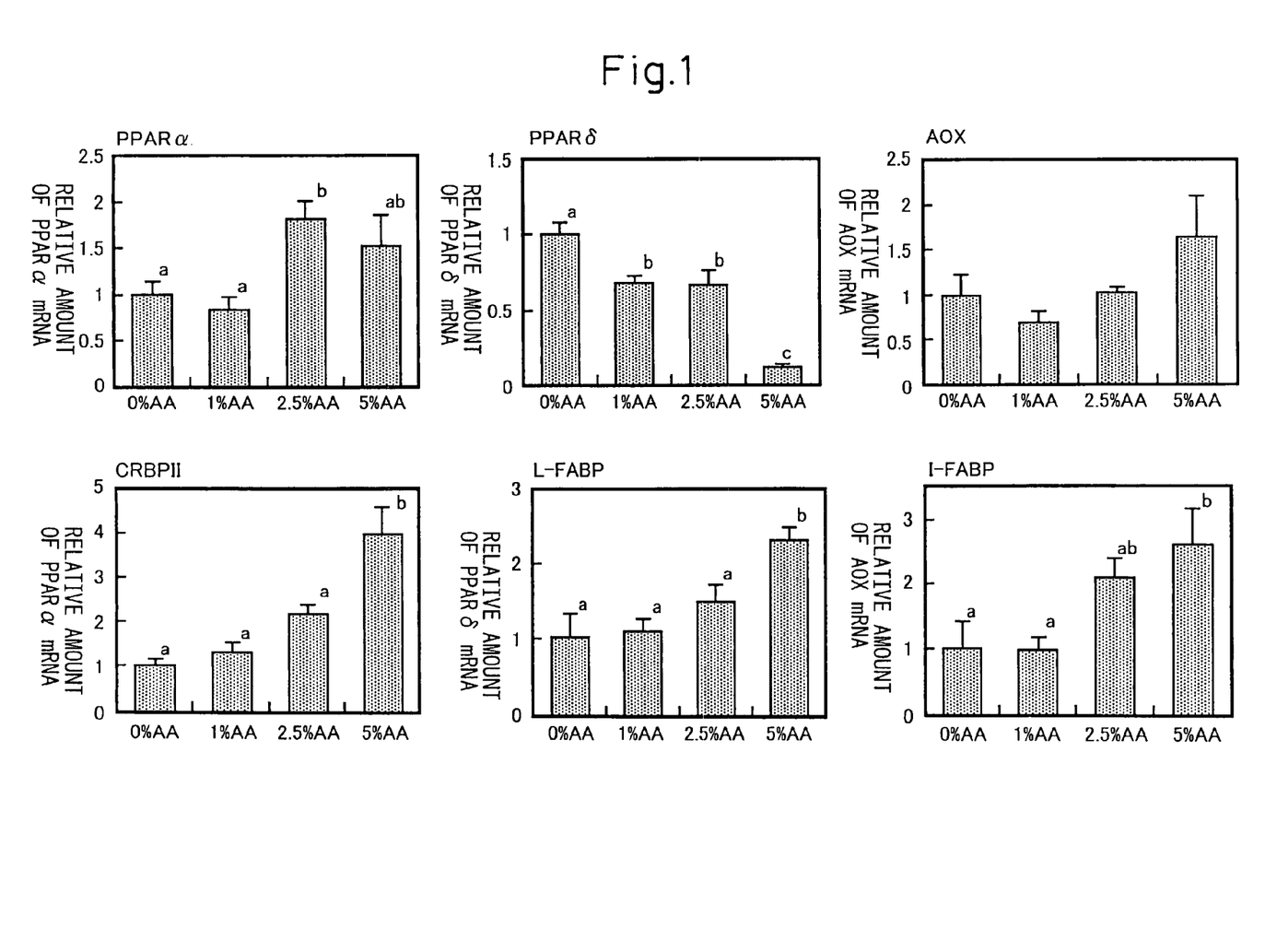
FIG. 1 shows the result of examining the influence of fat/oil where arachidonic acid was bonded to 2-position of a triglyceride(s) on rat jejunum PPAR and related gene expression. The results are expressed in terms of relative values (mean value±standard error, n=5) where 0% arachidonic acid food group was 1 after correction by the amount of internal standard gene 18SrRNA. a-c: Significant difference noted between different alphabets (p<0.05, Tukey). AOX: Acyl CoA Oxidase, CRBP II: Cellular Retinol-Binding Protein, Type II, L-FABP: Liver-type Fatty Acid-Binding Protein, I-FABP: Small Intestine-type Fatty Acid-Binding Protein.
Figure 2:
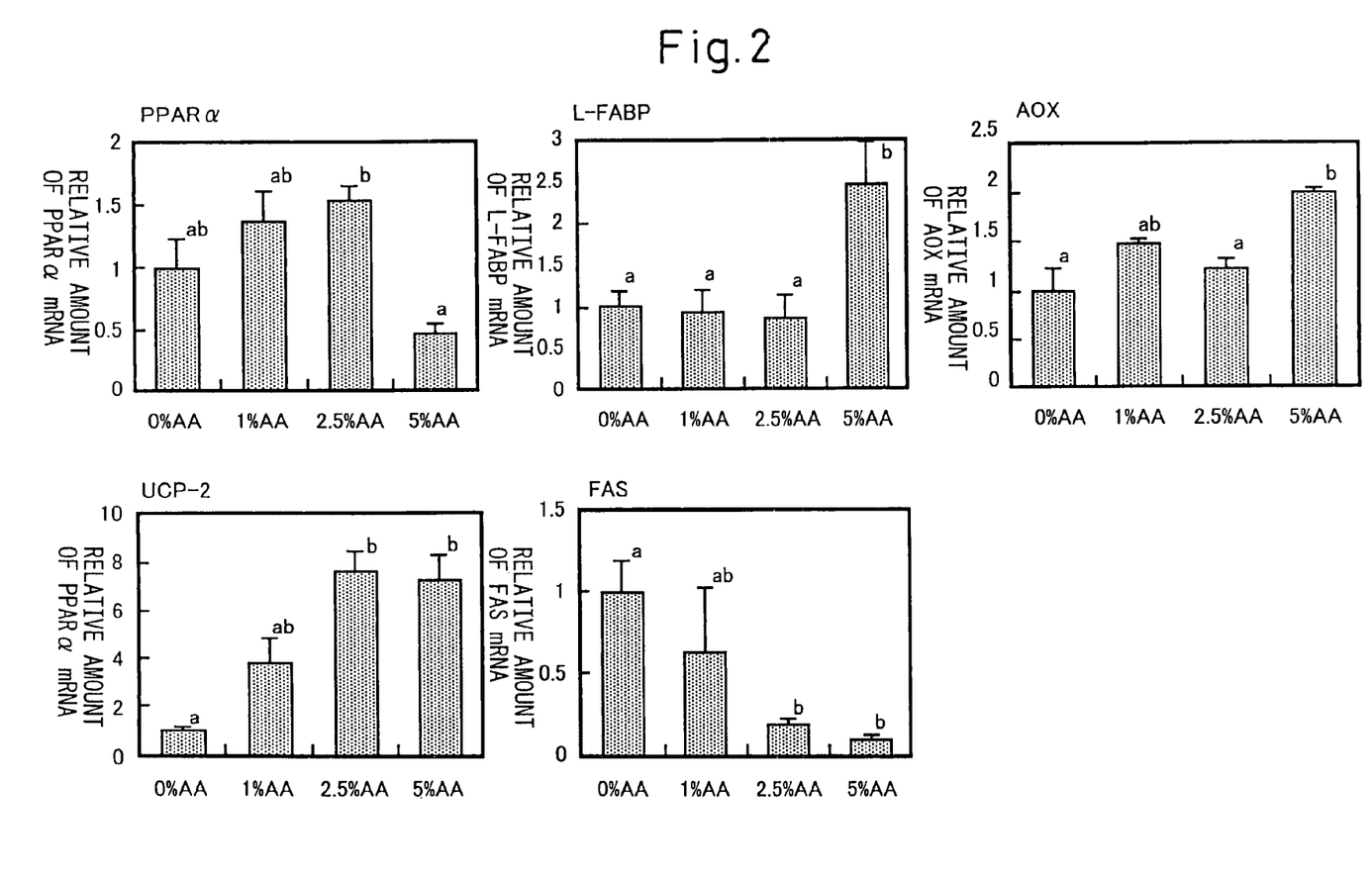
FIG. 2 shows the result of examining the influence of fat/oil where arachidonic acid was bonded to 2-position of a triglyceride(s) on rat liver PPAR and related gene expression. The results are expressed in terms of relative values (mean value±standard error, n=5) where 0% arachidonic acid food group was 1 after correction by the amount of internal standard gene 18SrRNA. a,b: Significant difference noted between different alphabets (p<0.05, Tukey). L-FABP: Liver-type Fatty Acid Binding Protein, AOX: Acyl CoA Oxidase, UCP-2: Decoupling Protein, FAS: Fatty Acid-Synthetase.
Figure 3:
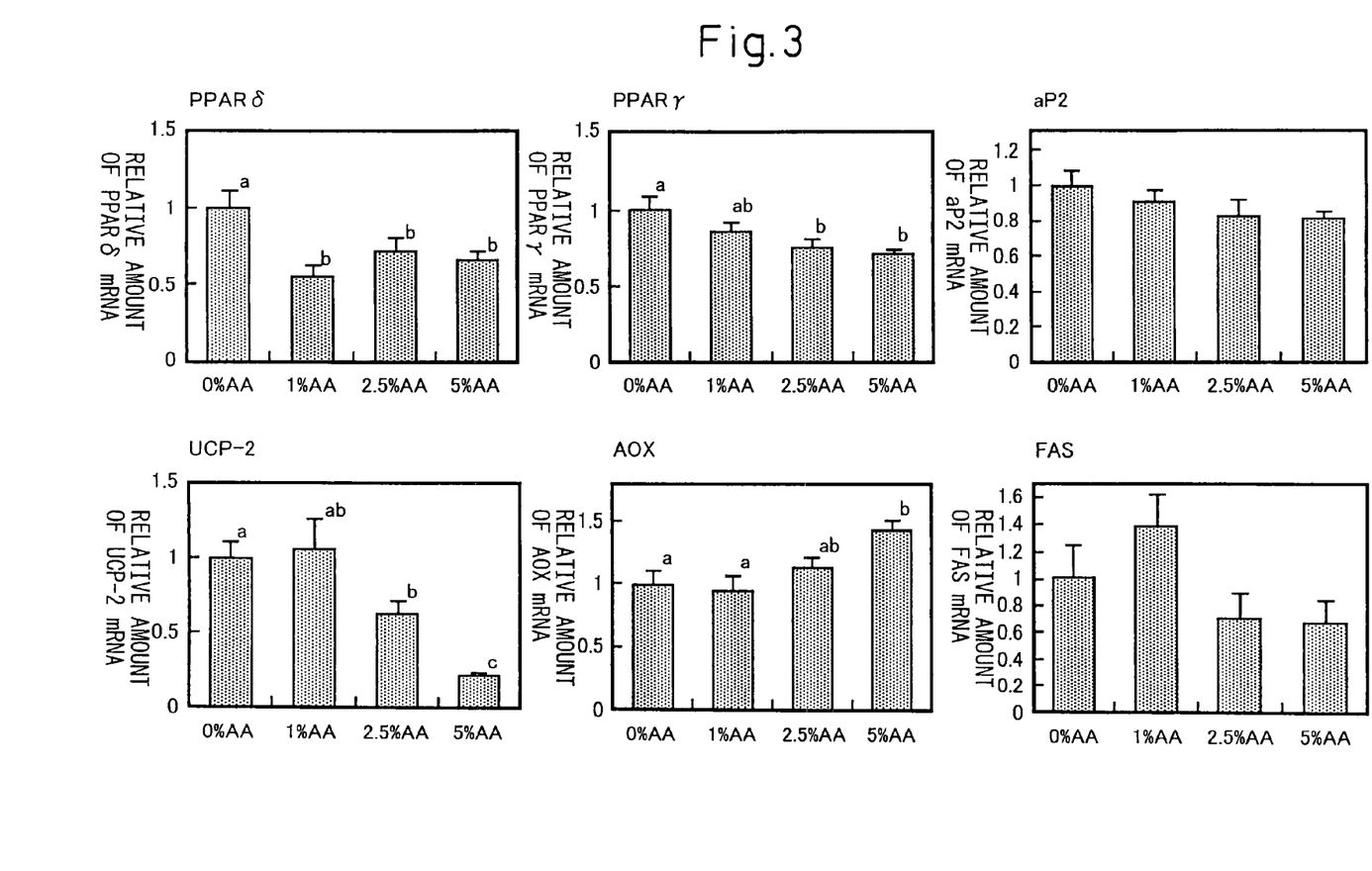
FIG. 3 shows the result of examining the influence of fat/oil where arachidonic acid was bonded to 2-position of a triglyceride(s) on rat epididymis PPAR and related gene expression. The results are expressed in terms of relative values (mean value±standard error, n=5) where 0% arachidonic acid food group was 1 after correction by the amount of internal standard gene 18SrRNA. a-c: Significant difference noted between different alphabets (p<0.05, Tukey). aP2: Fat Cell-Specific Fatty Acid-Binding Protein, UCP-2: Decoupling Protein, AOX: Acyl CoA Oxidase, FAS: Fatty Acid-Synthetase.

In jejunum of rats, expressed amount of PPARα mRNA increased to an extent of about 1.5- to 1.7-fold in the groups of 2.5% and 5% AA food (FIG. 1). On the other hand, expressed amount of PPARδ mRNA in jejunum lowered depending upon the arachidonic acid content in the feed. In addition, expressed amount of jejunum CRBP II, L-FABP, I-FABP and AOX mRNA which are target genes for PPARα increased depending upon the ingested arachidonic acid content. Since retinol which is absorbed in jejunum is a hydrophobic nutrient, most of it is present in cytoplasm as being bonded to a combined protein. A cellular retinol-bonded protein type II (CRBP II) plays an important role in intracellular transportation and esterification of retinol is.

Therefore, it is now apparent that arachidonic acid efficiently mediates absorption and metabolism of fat-soluble vitamins by way of an increase of expressed amount of PPAR a mRNA and an increase of expressed amount of jejunum CRBP II mRNA. From the above result, it has become clear that arachidonic acid ingested into small intestine functions as a ligand mainly for PPARα either directly or as a precursor for eicosanoids.

In liver, expressed amount of PPARα mRNA increased in a group of 1% AA food and a group of 2.5% AA food while, in a 5% AA food group, it decreased. However, expressed amounts of L-FABP, AOX and UCP-2 mRNA which are PPARα target genes increased depending upon the amounts of arachidonic acid and showed the highest value in a 5% AA food group. Although that is different from a variation pattern of PPARα mRNA, it can be said as a result that arachidonic acid activates the PPARα and adjusts the gene expression in a safe and effective manner until its amount reaches 2.5%. From the above, it has become clear that suppression of fatty acid synthesis system (not by way of PPAR) and promotion of fatty acid decomposition system accompanied by an increase of expressed amount of PPARα (by way of PPAR) are controlled in a genetic level and concentration of triglyceride(s) in blood is lowered.

In epididymis white fat tissues, expressed amounts of PPARα and PPARδ mRNA significantly lowered depending upon the amount of arachidonic acid. Further, expressed amount of fat cell-specific fatty acid bonded protein (aP2) mRNA also lowered depending upon the concentration. It has been known that PPARδ participates in differentiation and induction of fat cells and promotes the fat accumulation in white fat tissues, and a decrease of epididymis fat tissue weight by ingestion of arachidonic acid (Table 4) suppresses numbers and size of white fat cells or, in other words, differentiation and aging of fat cells by way of decrease of expressed amount of PPARδ mRNA. On the other hand, expressed amount of white fat tissue AOX mRNA increased as a result of increase of amount of arachidonic acid and, therefore, promotion of fatty acid decomposition system was also observed.

Example 5

Adjustment of Lipid Metabolism Gene Expression by Arachidonic Acid-containing Structured Lipid Influence of the structured lipid where arachidonic acid chemically synthesized in Example 2 as a constituting fatty acid on expression of lipid metabolism-related gene was investigated using rats. The effects were compared among PPP where palmitic acid (P) is bonded to 1,2,3-positions of a triglyceride(s), a mixture of same amounts of PPA where palmitic acid is bonded to 2-position and arachidonic acid is bonded to 3-position of a triglyceride(s) with APP where palmitic acid is bonded to 2,3(1)-positions and arachidonic acid is bonded to 1(3)-position of a triglyceride(s) (in chemical synthesis, it is a mixture of same amounts of PPA and APP and, hereinafter, such as mixture in the same amounts will be referred to as PPA for the sake of convenience) and PAP where palmitic acid is bonded to 1,3-positions and arachidonic acid is bonded to 2-position of a triglyceride(s) which are examples of the structured lipid.

Male rats of SD strain of 5 weeks age were divided into four groups each comprising five rats, acclimatized for one week with a standard solid feed and ingested for two weeks with an experimental food (10% PPA and 10% PAP; Table 5) compounded with 10% of arachidonic acid-containing structured lipid (PPA or PAP). In the control group, an experimental food (10% PPP) compounded with 10% of PPP was used. In ingestion of the food, a pair-feeding was conducted and body weight was measured every day. The experimental food was prepared using agar so that the daily ingested energy became same among each of the experimental food groups.

After two weeks from ingestion of the experimental food, rats were killed by decapitation and, according to the same method as in Example 4, each tissue was collected and total RNA was extracted and then analysis of gene expression was carried out by a northern blotting.

TABLE 5

Component Compositions of Experimental Food

|  | Low-Fat | 10% PPP | 10% PPA | 10% PAP |
|---|---|---|---|---|
|  |  | g/kg feed |  |  |
| Casein (Vitamin-free) | 157 | 157 | 157 | 157 |
| β-Corn starch | 526 | 301 | 301 | 301 |
| Corn oil | 23 | 24 | 24 | 24 |
| PPP |  | 100 |  |  |
| PPA |  |  | 100 |  |
| PAP |  |  |  | 100 |
| Minerals AIN-G93 | 28 | 28 | 28 | 28 |
| Vitamins AIN-93 | 8 | 8 | 8 | 8 |
| DL-Methionine | 2.4 | 2.4 | 2.4 | 2.4 |
| Choline bitartrate | 1.6 | 1.6 | 1.6 | 1.6 |
| 2% Agar | 253 | 378 | 378 | 378 |

Each of the feeds was added with 0.25 g/kg diet of α-tocopherol.

Influence of on tissue weight and serum lipid concentration after 2 weeks from ingestion of the experimental food is shown in Table 6. Serum triglyceride(s) concentration was significantly high in a group of 10% PPP food while, in the groups of 10% PPA and 10% PAP food, there was no significant difference from a low-fat food group. Although the same 10% fat/oil were added to a low-fat food (2.4% corn oil), serum triglyceride(s) significantly lowered showing the similar value as the low-fat good group when one of fatty acids binding to a triglyceride(s) was substituted with arachidonic acid. With regard to serum total cholesterol concentration, low values were noted in the groups of 10% PPA and 10% PAP foods as compared with a 10% PPP food group.

TABLE 6

Influence of Ingestion of Experimental Food on Body Weight Increase, Relative Tissue Weight and Serum Lipid Concentration in Rats

|  | Low-fat | 10% PPP | 10% PPA | 10% PAP |
|---|---|---|---|---|
| Body weight increase (g/14 days) | $71 \pm 5^{ab}$ | $61 \pm 5^{a}$ | $80 \pm 4^{b}$ | $67 \pm 5^{ab}$ |
| Liver weight (g/100 g body weight) | $4.4 \pm 0.3$ | $4.3 \pm 0.3$ | $4.2 \pm 0.1$ | $3.4 \pm 0.8$ |
| Serum triglyceride(s) concn (μmol/dl) | $191 \pm 32.3^{a}$ | $316 \pm 64.3^{b}$ | $173 \pm 6.6^{b}$ | $174 \pm 7.5^{b}$ |
| Serum total cholesterol concn (μmol/dl) | $235 \pm 7.8^{a}$ | $201 \pm 9.2^{a}$ | $150 \pm 16.6^{b}$ | $178 \pm 15.3^{ab}$ |

$^{a,b}$significant difference observed between different alphabets ($p < 0.05$)

Figure 4:
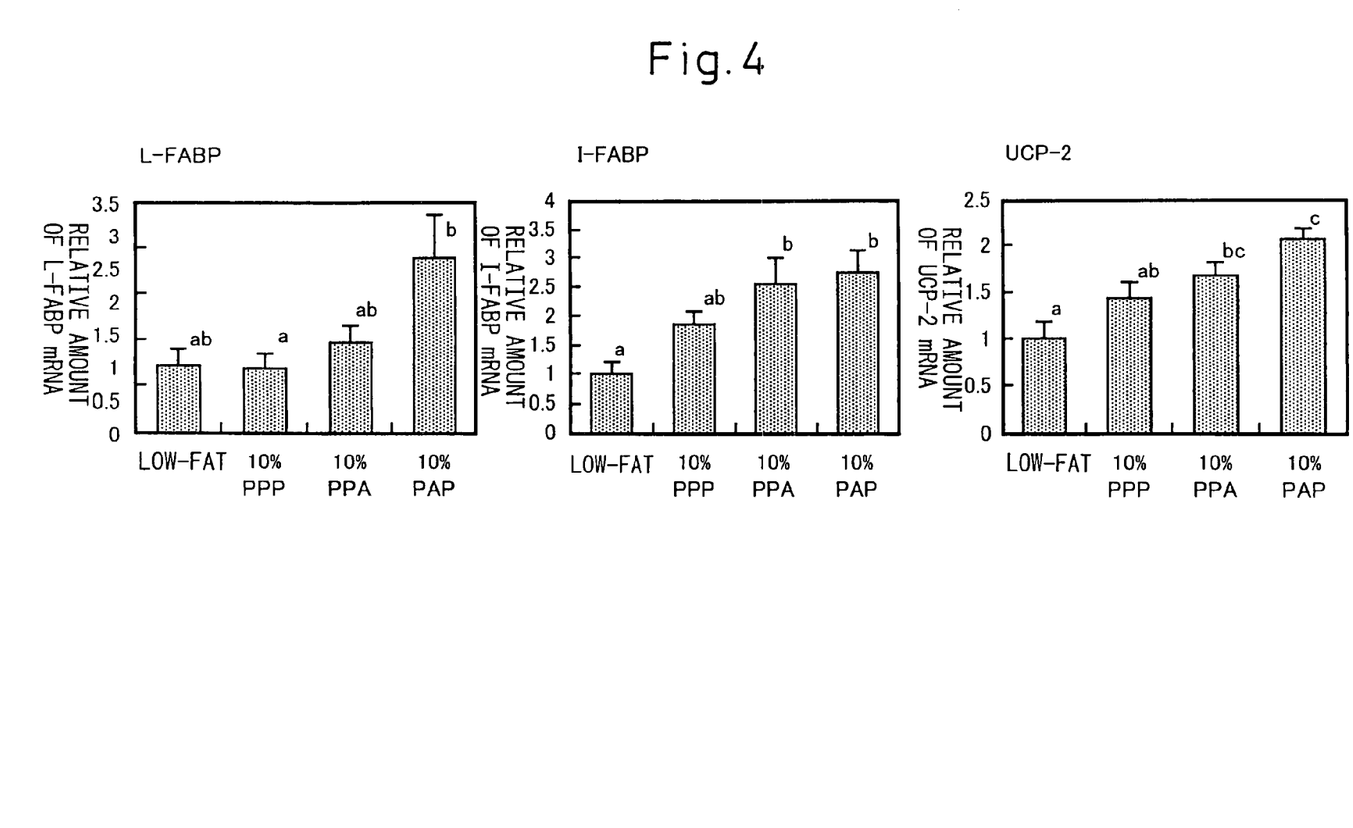
FIG. 4 shows the result of examining the influence of structured lipid containing arachidonic acid on rat liver PPAR and related gene expression. The results are expressed in terms of relative values (mean value±standard error, n=5) where 0% arachidonic acid food group was 1 after correction by the amount of internal standard gene 18SrRNA. a-c: Significant difference noted between different alphabets (p<0.05, Tukey). L-FABP: Liver-type Fatty Acid-Binding Protein, I-FABP: Small Intestine-type Fatty Acid-Binding Protein, UCP-2: Decoupling Protein.

Influence of structured lipid on expression of target gene of PPAR of jejunum is shown (FIG. 4). From PPA, each one molecule of palmitic acid and arachidonic acid is dissociated and absorbed by the action of pancreatic lipase specific to 1,3-positions and arachidonic acid having a particularly strong PPAR ligand activity acts as a PPARα ligand in small intestine and, therefore, expressed amount of target gene of PPAR increased in a group of 10% PPA food as compared with a PPP food group which is a control group. On the other hand, when it is considered that two molecules of dissociated palmitic acid and one molecule of 2-arachidonoyl monoglyceride (2-AG) are produced from PAP and are incorporated into epidermal cells of small intestine, it is assumed that, since palmitic acid has a weak action as a PPAR ligand, there will be almost no influence on the expression of target gene of PPAR in a group of 10% PAP food as compared with a group of PPP food which is a control group. However, the result was entirely the contrary being similar to or even more than the group of 10% PPA food.

Figure 5:
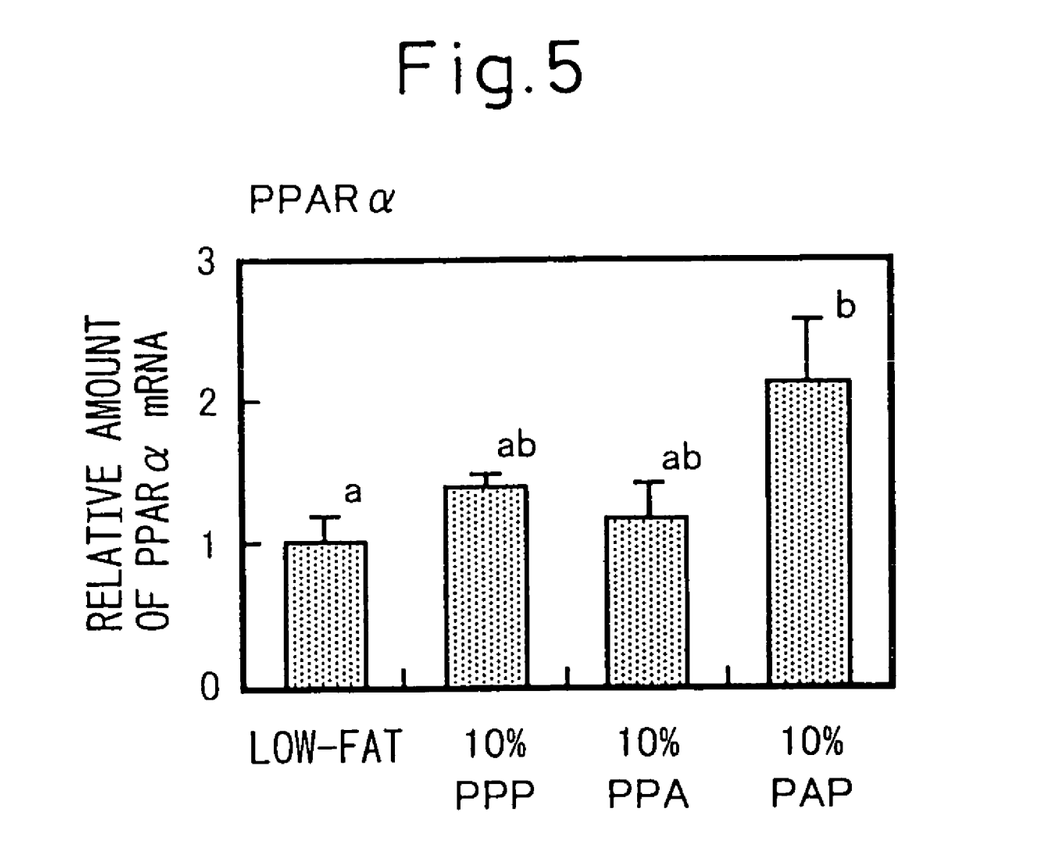
FIG. 5 shows the result of examining the influence of structured lipid containing arachidonic acid on rat epididymis white fat tissue PPAR and related gene expression. The results are expressed in terms of relative values (mean value±standard error, n=5) where 0% arachidonic acid food group was 1 after correction by the amount of internal standard gene 18SrRNA. a,b: Significant difference noted between different alphabets (p<0.05, Tukey).

Expressed amount of PPARα mRNA of liver significantly increased in a group of PAP food (FIG. 5). In jejunum, a significant action of a monoglyceride (2-AG) where arachidonic acid is bonded by the action of lipase specific to 1,3-positions was found and it was proved that the same effect was available in liver as well. Two molecules of palmitic acid and one molecule of 2-AG incorporated into epidermal cells of small intestine are reconstructed to a triglyceride(s) (in that case, although there is a possibility of bonding of other inherent fatty acids existing in the epidermal cells of the small intestine to 1,3-positions, arachidonic acid bonded to 2-position is retained), incorporated into chylomicron, transferred to peripheral tissues together with secretion of lymph and blood flow and finally incorporated into liver.

The result that PAP significantly increased the expressed amount of PPARα in the liver shows that a triglyceride(s) structure where arachidonic acid is bonded to 2-position is retained to an extent of liver and achieves the function and the significance of bonding of arachidonic acid, i.e. a poly-unsaturated fatty acid, at 2-position has been proved. As compared with a low-fat food where fat/oil load is 2.4%, the structured lipid load of 10% (total fat/oil load being 12.4%) of PPP, PPA and PAP foods is not an extreme fat load and, therefore, although there is no difference between PPA and PAP in view of serum triglyceride(s) concentration and serum total cholesterol concentration, there is a clear difference in a level of expression of gene whereby it is apparent that, in an extreme lipid load, PAP (a triglyceride(s) where a poly-unsaturated fatty acid is bonded to 2-position) significantly lowers the serum lipid concentration.

Example 6

Serum Lipid Lowering Action by Structured Lipid Containing Arachidonic Acid

Influence of arachidonic acid chemically synthesized in Example 2 on serum lipid lowering action of the constituting fatty acid was investigated in a high-fat foods. The effects were compared using structured lipids which were PPP, PPA and PAP being the same as in Example 5 as well as 8P8 where caprylic acid (8) is bonded to 1,3-positions and palmitic acid is bonded to 2-position of a triglyceride(s), a mixture of the same amounts of 88A where caprylic acid is bonded to 1,2-positions and arachidonic acid is bonded to 3-position of a triglyceride(s) with A88 where caprylic acid is bonded to 2,3-position and arachidonic acid is bonded to 1-position of a triglyceride(s) (a mixture of same amounts of 88A with A88 is prepared in chemical synthesis; such a mixture of same amounts of them will be referred to as 88A hereinafter for the sake of convenience) and 8A8 where caprylic acid is bonded to 1,3-positions and arachidonic acid is bonded to 2-position of a triglyceride(s).

Male rats of SD strain of 5 weeks age were divided into eight groups each comprising five rats, acclimatized for one week with a standard solid feed and ingested for two weeks with the experimental food as shown in Table 7 and Table 8 (normal, high-TG, 7.5% PPP, 7.5% PAP, 7.5% PPA, 7.5% 8P8, 7.5% 8A8 and 7.5% 88A). Incidentally, the condition for a high-fat food was that the rate of fat/oil in the feed was made 20%, beef tallow abundant in saturated fatty acid was used as a base and 2% of corn oil were compounded to avoid the deficiency of essential fatty acids. In the control group, an experimental food (high-TG food, 20% fat/oil food) compounded with 18% of 8P8 (20% as a result of addition of 2% of corn oil) was used.

After two weeks from ingestion of the experimental food, rats were killed by decapitation and triglyceride(s) concentration and total cholesterol concentration in a serum fraction were quantified using a measuring kit (Triglyceride(s) E-Test Wako and Total Cholesterol E-Test Wako being used, respectively).

TABLE 7

Component Composition of Experimental Food

|  | Normal Food | High-TG Food (20% Fat) | High-TG Food (7.5% PPP) g/kg Feed | High-TG Food (7.5% PAP) | High-TG Food (7.5% PPA) |
|---|---|---|---|---|---|
| Casein | 200 | 200 | 200 | 200 | 200 |
| DL-Methionine | 3 | 3 | 3 | 3 | 3 |
| Corn starch | 150 | 150 | 150 | 150 | 150 |
| Sucrose | 500 | 350 | 350 | 350 | 350 |
| Cellulose powder | 50 | 50 | 50 | 50 | 50 |
| Minerals AIN-76 | 35 | 35 | 35 | 35 | 35 |
| Vitamins AIN-76 | 10 | 10 | 10 | 10 | 10 |
| Choline bitartrate | 2 | 2 | 2 | 2 | 2 |
| Corn oil | 20 | 20 | 20 | 20 | 20 |
| Beef tallow | 30 | 180 | 105 | 105 | 105 |
| PPP |  |  | 75 |  |  |
| PAP |  |  |  | 75 |  |
| PPA |  |  |  |  | 76 |
| 8P8 |  |  |  |  |  |
| 8A8 |  |  |  |  |  |
| 88A |  |  |  |  |  |

TABLE 8

Component Composition of Experimental Food

|  | High-TG Food (7.5% 8P8) | High-TG Food (7.5% 8A8) g/kg Feed | High-TG Food (7.5% 88A) |
|---|---|---|---|
| Casein | 200 | 200 | 200 |
| DL-Methionine | 3 | 3 | 3 |
| Corn starch | 150 | 150 | 150 |
| Sucrose | 350 | 350 | 350 |
| Cellulose powder | 50 | 50 | 50 |
| Minerals AIN-76 | 35 | 35 | 35 |
| Vitamins AIN-76 | 10 | 10 | 10 |
| Choline bitartrate | 2 | 2 | 2 |
| Corn oil | 20 | 20 | 20 |
| Beef tallow | 105 | 105 | 105 |
| PPP |  |  |  |
| PAP |  |  |  |
| PPA |  |  |  |
| 8P8 | 75 |  |  |
| 8A8 |  | 75 |  |
| 88A |  |  | 75 |

Influences after two weeks from ingestion of the experimental food on tissue weight and serum lipid concentration are shown in Table 9. Serum triglyceride(s) concentration showed significantly high values in a high-triglyceride(s) food group. Although a 7.5% PPP food group which is a control group showed no change at all, a 7.5% PPA food group and a 7.5% PAP food group significantly lowered the serum triglyceride(s). With regard to the effects of PAP and PPA, a 7.5% PAP food group showed significantly low values. Similar result was also shown in structured lipid groups (7.5% 8P8, 7.5% 8A8 and 7.5% 88A) where caprylic acid is a constituting fatty acid. It has been confirmed that, when a medium-chain fatty is used as a constituting fatty acid, an effect of lowering the serum triglyceride(s) is able to be significantly enhanced. Similar result was also found concerning serum total cholesterol concentration.

It has been known that not only arachidonic acid but also poly-unsaturated fatty acids adjust the serum triglyceride(s) concentration and the serum cholesterol concentration by way of PPAR and it is apparent that, like in the case of bonding of arachidonic acid to 2-position, the similar effect is achieved in the structured lipid to which a poly-unsaturated fatty acid is bonded to 2-position.

TABLE 9

Influence of Ingestion of Experimental Food on Serum Lipid Concentration

|  | Normal Food | High-TG Food (20% Fat) | High-TG Food (7.5% PPP) | High-TG Food (7.5% PAP) |
|---|---|---|---|---|
| Serum Triglyceride(s) Concn (μmol/dl) | $45.0 \pm 5.9^a$ | $103.0 \pm 5.6^b$ | $109.2 \pm 6.8^b$ | $80.4 \pm 3.9^a$ |
| Serum Total Cholesterol Concn (μmol/dl) | $80.2 \pm 2.8^a$ | $102.4 \pm 4.9^b$ | $104.3 \pm 5.9^b$ | $91.7 \pm 3.3^a$ |

|  | Normal Food | High-TG Food (7.5% PPA) | High-TG Food (7.5% 8P8) | High-TG Food (7.5% 8A8) | High-TG Food (7.5% 88A) |
|---|---|---|---|---|---|
| Serum Triglyceride(s) Concn (μmol/dl) |  | $93.1 \pm 1.3^a$ | $101.8 \pm 5.3^b$ | $63.3 \pm 4.1^a$ | $83.1 \pm 3.6^a$ |

TABLE 9-continued

Influence of Ingestion of
Experimental Food on Serum Lipid Concentration

| Serum Total Cholesterol Concn (μmol/dl) | $92.4 \pm 4.9^a$ | $99.7 \pm 4.2^b$ | $85.6 \pm 2.5^b$ | $92.9 \pm 2.9^a$ |
|---|---|---|---|---|

$^{a,b}$significant difference observed between different alphabets (p < 0.05)

Example 7

Example for Preparation of Capsules Compounded with Fat/Oil (Triglyceride(s)) where Arachidonic Acid is Bonded to 2-position of Triglyceride(s)

Gelatin (100 parts by weight) and 35 parts by weight of glyceride for food additive were dissolved in water at 50 to 60° C. to prepare a gelatin film having a viscosity of 2,000 cp. Then the fat/oil (triglyceride(s)) prepared in Example 1 where arachidonic acid is bonded to 2-position of triglyceride(s) was mixed with 0.05% by weight of vitamin E oil to prepare a content 1. Vitamin E oil (0.05% by weight) was compounded with the fat (triglyceride(s)) prepared in Example 3 where 32 mol % of 8A8 were contained to prepare a content 2. Capsule formation and drying were carried out by a conventional method using those contents 1 and 2 to prepare soft capsules each containing 200 mg of the content.

Example 8

Serum Lipid Improving Action in Humans After Ingestion of Fat (Triglyceride(s)) where Arachidonic Acid is Bonded to 2-position of Triglyceride(s)

The test of the present invention to humans was carried out with careful consideration following the spirit of the Helsinki Declaration. Firstly, explanation for consent in joining the test was conducted and six capsules of the fat/oil where arachidonic acid was bonded to 2-position of triglyceride(s) prepared in Example 7 (80 mg/capsule in terms of arachidonic acid) were ingested for one months to eight people who consented. Before and after ingestion of the capsules, blood was collected and blood biochemical markers were analyzed.

Result of the measurement is shown in Table 10. The serum triglyceride(s) concentration significantly lowered by ingestion of the capsules. Although the serum cholesterol concentration significantly increased, that was not due to an increase of concentration of LDL-cholesterol which was the bad cholesterol but due to a significant increase of concentration of HDL-cholesterol which was the good cholesterol. From the above, it has been confirmed that serum lipid is improved by the fat/oil where arachidonic acid is bonded to 2-position of a triglyceride(s).

TABLE 10

Result of Physical Examination Before and
After Ingestion of Capsules of Fat/Oil where Arachidonic
Acid is Binding to 2-Position of Triglyceride(s)

| | Before | After |
|---|---|---|
| Height (cm) | $169.8 \pm 5.9$ | $169.8 \pm 5.9$ |
| Body Weight (kg) | $65.1 \pm 6.5$ | $65.0 \pm 5.9$ |
| Neutral Fat/Oil (Triglyceride(s)) | $99.4 \pm 28.0^a$ | $74.1 \pm 17.5^b$ |
| Total Cholesterol | $175.9 \pm 17.6^a$ | $184.9 \pm 18.6^b$ |
| HDL-Cholesterol | $58.5 \pm 10.2^a$ | $63.1 \pm 10.0^b$ |
| LDL-Cholesterol | $106.9 \pm 19.4$ | $108.3 \pm 17.6$ |

$^{a,b}$significant difference observed between different alphabets (p < 0.05)

Example 9

Serum Triglyceride(s) Lowering Action in Humans After Ingestion of Capsules of Edible Fat/Oil Containing 8A8

Explanation for the consent of joining the test was conducted as same as in Example 8 and three capsules of the edible fat/oil containing 8A8 prepared in Example 7 (72 mg/capsule in terms of arachidonic acid) were ingested for one months to eight people who consented. Before and after ingestion of the capsules, serum triglyceride(s) concentration was analyzed whereupon it showed significant lowering from 162±29.3 to 83.3±14.9.

Example 10

Use for Fat Transfusion Preparation

The fat/oil (triglyceride(s)) containing 96% of 8A8 prepared in Example 3 (400 g), 48 g of pure egg yolk lecithin, 20 g of oleic acid, 100 g of glyceride and 40 ml of 0.1N sodium hydroxide were mixed and homogenized and then distilled water for injection was added thereto to make 4 liters. This was emulsified using a high-pressure spraying emulsifier to prepare a lipid emulsion. Each 200 ml of the lipid emulsion was disposed into a bag made of plastic and sterilized with a high-pressure steam at 121° C. for 20 minutes to give a fat transfusion preparation.

Example 11

Use for Juice

β-Cyclodextrin (2 g) was added to 20 ml of a 20% aqueous solution of ethanol, 100 mg of the fat/oil where arachidonic acid was bonded to 2-position of a triglyceride(s) (compounded with 0.05% of vitamin E) prepared in Example 1 were added thereto and the mixture was incubated at 50° C. for 2 hours. After cooling to room temperature (for about 1 hour), incubation was further conducted at 4° C. for 10 hours together with stirring. The resulting precipitate was recovered by centrifugal separation, washed with n-hexane and freeze-dried to give 1.8 g of an inclusion compound of cyclodextrin containing the fat/oil where arachidonic acid was bonded to 2-position of a triglyceride(s). The powder (1 g) was homogeneously mixed with 10 liters of juice to prepare a juice which contained the fat/oil where arachidonic acid was bonded to 2-position of a triglyceride(s).

The invention claimed is:

1. A food composition which contains a triglyceride(s) where a poly-unsaturated fatty acid is bonded to 2-position of the triglyceride(s) saturated fatty acid and/or mono-unsaturated fatty acid are/is bonded to 1,3-positions of the triglyceride(s) in such a manner that a daily ingested amount of the triglyceride(s) for an adult per day is made 0.001 to 20 g in terms of the amount of the poly-unsaturated fatty acid.

2. The food composition according to claim 1, wherein the composition contains a triglyceride(s) where arachidonic acid is bonded to 2-position and saturated fatty acid and/or mono-unsaturated fatty acid are/is bonded to 1,3-positions of the triglyceride(s) in such a manner that a daily ingested amount of the triglyceride(s) where arachidonic acid is bonded to 2-position and saturated fatty acid and/or mono-unsaturated fatty acid are/is bonded to 1,3-positions of the triglyceride(s) for an adult per day in made 0.001 to 20 g in terms of the amount of arachidonic acid.

* * * * *